(12) United States Patent
Nakaji et al.

(10) Patent No.: US 9,179,842 B2
(45) Date of Patent: Nov. 10, 2015

(54) OPTICAL TOMOGRAPHY DEVICE

(75) Inventors: Haruo Nakaji, Boston, MA (US);
Hidenao Fukuyama, Kyoto (JP);
Yuusuke Iso, Kyoto (JP); Shinichi Urayama, Kyoto (JP); Naoya Oishi, Kyoto (JP); Hiroshi Fujiwara, Kyoto (JP)

(73) Assignees: Sumitomo Electric Industries, Ltd., Osaka-shi (JP); Kyoto University, Kyoto-shi (JP)

( * ) Notice: Subject to any disclaimer, the term of this patent is extended or adjusted under 35 U.S.C. 154(b) by 73 days.

(21) Appl. No.: 14/116,732

(22) PCT Filed: May 9, 2012

(86) PCT No.: PCT/JP2012/061892
§ 371 (c)(1),
(2), (4) Date: Feb. 4, 2014

(87) PCT Pub. No.: WO2012/153769
PCT Pub. Date: Nov. 15, 2012

(65) Prior Publication Data
US 2014/0168657 A1    Jun. 19, 2014

(30) Foreign Application Priority Data

May 10, 2011    (JP) ................................ P2011-105488

(51) Int. Cl.
*G01B 9/02*    (2006.01)
*A61B 5/00*    (2006.01)
(Continued)

(52) U.S. Cl.
CPC ........... *A61B 5/0073* (2013.01); *A61B 10/0041* (2013.01); *G01B 9/02091* (2013.01); *G01N 21/4795* (2013.01)

(58) Field of Classification Search
CPC ............. A61B 5/0073; A61B 10/0041; G01B 9/02091; G01N 21/3563; G01N 21/359; G01N 21/4795
See application file for complete search history.

(56) References Cited

U.S. PATENT DOCUMENTS 6,075,610 A *  6/2000  Ueda et al. .................... 356/432
6,335,792 B1 * 1/2002  Tsuchiya ...................... 356/432
(Continued)

FOREIGN PATENT DOCUMENTS

JP    2003-528291 A    9/2003
JP    2007-085775 A    4/2007
(Continued)

OTHER PUBLICATIONS

Extended European Search Report in European Patent Application No. 12781890.4, dated Sep. 19, 2014.
(Continued)

*Primary Examiner* — Michael A Lyons
(74) *Attorney, Agent, or Firm* — Venable LLP; Michael A. Sartori; F. Brock Riggs

(57) ABSTRACT

An optical tomography device 1 is provided as one capable of obtaining tomographic information of a measuring object with higher accuracy. In the optical tomography device 1, numerical apertures of reception fibers 12, 13 are different from each other. Therefore, the device has a configuration wherein the reception fibers 12, 13 receive two kinds of respective light beams with different solid angle distributions, whereby the device can also obtain angular information, in addition to intensity information of light emerging from a measuring object 100. As a result, the accuracy is enhanced for an analysis about the tomographic information of the measuring object.

9 Claims, 3 Drawing Sheets

(51) Int. Cl.
*G01N 21/47* (2006.01)
*A61B 10/00* (2006.01)

(56) References Cited

U.S. PATENT DOCUMENTS

| | | | |
|---|---|---|---|
| 6,381,480 B1 * | 4/2002 | Stoddart et al. | 600/338 |
| 8,131,348 B2 | 3/2012 | Backman et al. | |
| 2002/0107448 A1 | 8/2002 | Gandjbakhche et al. | |
| 2003/0191398 A1 | 10/2003 | Motz et al. | |
| 2006/0058683 A1 * | 3/2006 | Chance | 600/476 |
| 2007/0129615 A1 | 6/2007 | Backman et al. | |
| 2007/0179368 A1 | 8/2007 | Backman et al. | |
| 2009/0009759 A1 | 1/2009 | Backman et al. | |
| 2009/0148945 A1 | 6/2009 | Ameer et al. | |
| 2009/0203977 A1 | 8/2009 | Backman et al. | |
| 2009/0234204 A1 | 9/2009 | Ridder et al. | |
| 2009/0325859 A1 | 12/2009 | Ameer et al. | |
| 2012/0176613 A1 * | 7/2012 | Marple et al. | 356/301 |

FOREIGN PATENT DOCUMENTS

| | | |
|---|---|---|
| JP | 2009-537285 A | 10/2009 |
| JP | 2010-236973 A | 10/2010 |
| WO | WO-2007/067163 A1 | 6/2007 |
| WO | WO-2007/136880 A2 | 11/2007 |

OTHER PUBLICATIONS

C.K. Hayakawa et al., "Use of the $\delta$-$P_1$ approximation for recovery of optical absorption, scattering, and asymmetry coefficients in turbid media," Applied Optics, vol. 43, No. 24 (2004), pp. 4677-4684.

International Search Report in PCT International Application No. PCT/JP2012/061892, dated Jun. 12, 2012.

International Preliminary Report on Patentability and Written Opinion in PCT International Application No. PCT/JP2012/061892, dated Nov. 21, 2013.

* cited by examiner

US 9,179,842 B2

OPTICAL TOMOGRAPHY DEVICE

TECHNICAL FIELD

The present invention relates to an optical tomography device.

BACKGROUND ART

Diffuse optical tomography using near-infrared light with sufficient safety and high permeability for living organisms is known as a method for obtaining tomographic information of living organisms. Since the near-infrared light used in this diffuse optical tomography, unlike X-rays, has very low invasiveness for living organisms and shows significantly different spectral characteristics in the frequency band of near-infrared light depending upon materials in the organisms, there are advantages including one such that various pieces of metabolic information of biological matter such as oxygen can be collected in high temporal resolution. A measuring device using this diffuse optical tomography is compact and inexpensive per se and is less stressful for a person as measuring subject; e.g., there is no need for the measuring subject to maintain a posture during measurement. Therefore, various studies have been conducted with expectations of application to more detailed analyses of vital functions and research is under way on an analysis method and others for obtaining tomographic information of living organism from the result obtained by irradiating a measuring object with near-infrared light (e.g., cf. Patent Literature 1).

CITATION LIST

Patent Literature

Patent Literature 1: Japanese Translation of PCT International Application Publication No. 2003-528291

SUMMARY OF INVENTION

Technical Problem

However, since the near-infrared light is considerably scattered in a living organism, the light incident into the living organism diffuses before emerging from the living organism, with the result that little spatial information is obtained from the received result of the light emerging from the living organism as measuring object, which raises possibilities that a long time is necessary for an analysis of parameters in a governing equation (e.g., a scattering coefficient and an absorption coefficient) of each part in the living organism from the received result of near-infrared light and that the accuracy of the analysis result becomes lower.

The present invention has been accomplished in view of the above circumstances and it is an object of the present invention to provide an optical tomography device capable of obtaining the tomographic information of the measuring object with higher accuracy.

Solution to Problem

In order to achieve the above object, an optical tomography device according to one aspect of the present invention is one comprising: a light source; an irradiation fiber for irradiating a measuring object with light from the light source; a receiving fiber for receiving light emerging from the measuring object in conjunction with irradiation with the light from the irradiation fiber; a detection unit for detecting an intensity of the light received from the receiving fiber; and an analysis unit for obtaining an optical characteristic value of an interior of the measuring object, based on the intensity of the light detected by the detection unit, wherein at least one of the irradiation fiber and the receiving fiber is a bundle in which a plurality of optical fibers are bundled together, and wherein the plurality of optical fibers have two or more kinds of numerical apertures.

In the above-described optical tomography device, when the irradiation fiber has two or more different numerical apertures, the measuring object can be irradiated in different ranges. When the receiving fiber has two or more different numerical apertures, the light can be received from different ranges of the measuring object. By adopting the configuration wherein two or more kinds of light beams with different solid angle distributions are radiated or received, it becomes feasible to obtain angular information, in addition of the intensity information of the light from the measuring object and, as a result, it can enhance the accuracy of the analysis about the tomographic information of the measuring object.

The device can be configured in a mode wherein the analysis unit applies the result obtained by the detection unit, to a transport equation as a governing equation governing propagation of light in the measuring object, thereby obtaining the optical characteristic value of the interior of the measuring object.

The angular information of the light from the measuring object can be most effectively utilized in performing the analysis using the transport equation. Therefore, when the analysis is conducted using the transport equation, the accuracy of the analysis can be more enhanced.

Specific examples of configurations for effectively achieving the above action include a mode wherein the optical characteristic value is an absorption coefficient of the interior of the measuring object. Another example can be a mode wherein the optical characteristic value is a scattering coefficient of the interior of the measuring object. A further example can be a mode wherein the optical characteristic value is an anisotropic scattering parameter of the interior of the measuring object.

The optical tomography device according to one aspect of the present invention can be configured in a mode wherein the analysis unit obtains an average of the optical characteristic value in the interior of the measuring object, and a distribution of the optical characteristic value in the interior of the measuring object.

The device can be configured in a mode wherein the irradiation fiber is the bundle in which the plurality of optical fibers are bundled together, and wherein the optical tomography device comprises a plurality of irradiation fibers. In this case, since there are the plurality of irradiation fibers provided, the irradiation position of the light can be readily changed and, as a result, the accuracy can be enhanced for the tomographic information obtained by the analysis.

The device can be configured in a mode wherein the receiving fiber is the bundle in which the plurality of optical fibers are bundled together, and wherein the optical tomography device comprises a plurality of receiving fibers. In this case, the reception position of the light from the measuring object can be readily changed and, as a result, the accuracy can be enhanced for the tomographic information obtained by the analysis.

The device can be configured in a mode wherein each of the irradiation fiber and the receiving fiber is connected to the light source or the detection unit, and wherein a path switching device implements switching between connections to the light source and to the detection unit. In this case, the functions of the irradiation fiber and the receiving fiber can be interchanged with each other, so as to enable change in irradiation position and reception position by the simple configuration.

The irradiation fiber and the receiving fiber are characterized by being bundled together in a bundle. In the case of this configuration, it becomes feasible to simplify the optical tomography device.

Advantageous Effect of Invention

One aspect of the present invention provides the optical tomography device capable of obtaining the tomographic information of the measuring object with higher accuracy.

DESCRIPTION OF EMBODIMENTS

An embodiment of the present invention will be described below in detail with reference to the drawings. The same elements will be denoted by the same reference signs in the description of the drawings, without redundant description.

Figure 1:
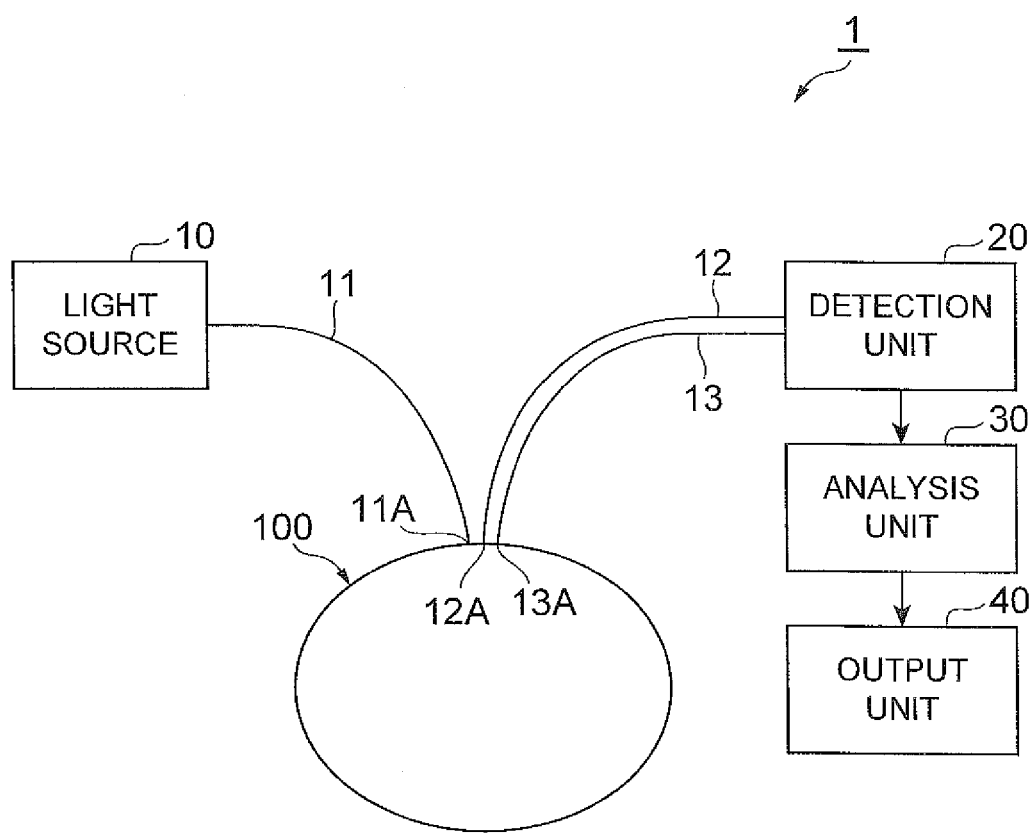
FIG. 1 is a drawing to illustrate a configuration of an optical tomography device.

FIG. 1 is a drawing to illustrate a configuration of an optical tomography device according to the present embodiment. The optical tomography device 1 has a function to irradiate a measuring object with near-infrared light, receive and analyze light emerging from the measuring object as a consequence of the irradiation, and construct and output a tomographic image of the measuring object on the basis of the analysis result. As shown in FIG. 1, the optical tomography device 1 of the present embodiment is configured including a light source 10, an irradiation fiber 11, receiving fibers 12, 13, a detection unit 20, an analysis unit 30, and an output unit 40. A measuring object 100 to be measured by the optical tomography device 1 is shown in FIG. 1.

The measuring object 100 to be measured by the optical tomography device 1 of the present embodiment is, for example, a head of a living organism and, when the head of the living organism is the measuring object, MR (Magnetic Resonance) information to be acquired is information that specifies an internal structure of the head inside this measuring object. When the measuring object is the head of the living organism, the MR information includes information specifying an appearance configuration of the head, and information specifying spatial distributions of internal tissues of the head such as the epidermis, skull, cerebrospinal fluid, brain parenchyma (gray matter and white matter), and vascular structure (arteries and veins).

The light source 10 emits light to irradiate the measuring object 100. Light of wavelengths transmitted by the measuring object 100 is used as the light emitted from the light source 10 and, when the measuring object 100 is the head of the living organism, the light to be used is near-infrared light at wavelengths of 700 to 2500 nm (wavelengths of not less than 700 nm and not more than 2500 nm). The device can be configured in a mode in which the light, before emitted from this light source 10, is modulated at a certain specified frequency by a chopper or the like. The light emitted from the light source 10 propagates through the irradiation fiber 11 as an optical fiber optically connected to the light source 10 and is injected into the measuring object 100 from an exit end 11A of the irradiation fiber 11.

With the injection of the light from the light source 10 into the measuring object 100, light emerging from the measuring object 100 enters the receiving fibers 12, 13 through entrance ends 12A, 13A of the receiving fibers 12, 13 and propagates through the receiving fibers 12, 13 to be detected by the detection unit 20. The receiving fibers 12, 13 to be used herein are optical fibers with different numerical apertures. An example thereof applied herein is such that the receiving fiber 12 has the numerical aperture NA of 0.8 (reception angles of ±53°, i.e., reception angles in the range of not less than −53° and not more than +53°) and the receiving fiber 13 has the numerical aperture NA of 0.7 (reception angles of ±44°, i.e., reception angles in the range of not less than −44° and not more than +44°). These receiving fibers 12, 13 are bundled together in a bundle (or integrated in a bundle). It is also possible to adopt a device configuration using a plurality of bundles of receiving fibers 12, 13. FIG. 1 shows the irradiation fiber 11 and the receiving fibers 12, 13 as separated from each other, but these may be bundled together into a bundle.

The detection unit 20 detects the intensities of the light beams received by the receiving fibers 12, 13. A lock-in amplifier is used as the detection unit 20. The light incident into the receiving fibers 12, 13 after emitted to the outside out of the light scattered inside the measuring object 100 is received by a photodetector such as a photomultiplier tube or an avalanche photodiode provided in the detection unit 20. The power of the received light is converted into an electric signal (voltage) and the electric signal includes noise or the like. In the case where the light emitted from the light source 10 is modulated at the specified frequency, the lock-in amplifier is used to extract only the specified-frequency component from the electric signal including a lot of noise or the like. This allows detection of weak light. Information about the electric signal detected by the detection unit 20 is fed to the analysis unit 30.

The analysis unit 30 analyzes optical characteristic values of the interior of the measuring object 100, based on measured values acquired by the detection unit 20. Specifically, the analysis unit 30 applies the result acquired by the detection unit 20 to the transport equation as a governing equation governing propagation of light in the measuring object, to obtain the optical characteristic values of the interior of the measuring object 100. Examples of the optical characteristic values include a scattering coefficient, an absorption coefficient, and an anisotropic scattering parameter. It is also possible to adopt a mode of calculating averages of optical characteristic values in the interior of the measuring object 100, and further obtaining distributions of the optical characteristic values in the interior of the measuring object 100, i.e., determining a structure of the interior of the measuring object 100 from the distributions of the optical characteristic values. The result of the analysis in the analysis unit 30 is fed to the output unit 40. The analysis unit 30 is provided with a CPU and memories (ROM and RAM or the like) and in the analysis unit 30 the CPU executes a computer program stored in the memory (e.g., a process shown in the flowchart of FIG. 2), thereby to execute the process of analyzing the optical characteristic values of the interior of the measuring object 100.

The output unit 40 outputs the analysis result acquired by the analysis unit 30 to the outside. Examples of methods for outputting the analysis result to the outside include a method of displaying the result on a display device such as a monitor, a method of outputting the result to a printer or the like, a method of outputting the result as electronic data, and so forth.

The analysis in the analysis unit 30 will be described below. It is known that propagation of light in a measuring object with incidence of light into the measuring object is governed by an equation that describes motion of particles, called the transport equation. Then, use of this transport equation allows us to accurately model a relation between the light incident into the measuring object and the light emerging from the measuring object with incidence of the light. Therefore, by applying correct values of the scattering coefficient and absorption coefficient suitable for a tissue of each part to this transport equation, the light emerging from the measuring object with incidence of specific light into the measuring object can be accurately calculated.

The transport equation used in the analysis in the analysis unit 30 can be represented by the expression (Math 1) below. In the below expression, $\mu_s$ represents the scattering coefficient and $\mu_a$ the absorption coefficient. Furthermore, g corresponds to the anisotropic scattering parameter.

$$\frac{1}{c}\frac{\partial I(\vec{r},\hat{s},t)}{\partial t} + \hat{s}\cdot\nabla I(\vec{r},\hat{s},t) + \mu_t I(\vec{r},\hat{s},t) = \quad [\text{Math 1}]$$

$$\mu_s \int_{4\pi} A(\hat{s}'\cdot\hat{s})I(\vec{r},\hat{s}',t)d\Omega' + S(\vec{r},\hat{s},t)$$

c: speed of light in substance
$\mu_t = \mu_s + \mu_a$: sum of scattering coefficient and absorption coefficient
$A(\hat{s}',\hat{s})$: phase function $$\left(g = \int_{4\pi}(\hat{s}',\hat{s})A(\hat{s}',\hat{s})d\Omega\right):$$

degree of anisotropy of scattering)
$S(\vec{r},\hat{s},t)$: internal light source
$I(\vec{r},\hat{s},t)$: intensity of light
$\vec{r}$: positional vector
$\hat{s}$: directional vector
$\hat{s}'$: directional vector about scattering
t: time
$\Omega'$: solid angle In the optical tomography device 1 of the present embodiment, the two receiving fibers 12, 13 with different numerical apertures are bundled and this bundle is used in measurement of scattered light. As an example, an optical fiber with NA=0.8 is used as the receiving fiber 12 and an optical fiber with NA=0.7 as the receiving fiber 13. Since the receiving fiber 12 has the reception angles of ±53° (in the range of not less than −53° and not more than +53°), scattered light within this angle range is received. Since the receiving fiber 13 has the reception angles of ±44° (in the range of not less than −44° and not more than) +44°, scattered light within this angle range is received. As a result, when a difference is calculated between powers of the light received by the receiving fiber 12 and the light received by the receiving fiber 13, an optical power of angular components larger than ±44° (the range of not less than −44° and not more than +44°) but smaller than ±53° (the range of not less than −53° and not more than +53°) can be calculated.

When the transport equation is to be used as a governing equation, the intensity of light is expressed by a function of positional vector, directional vector, and time and for this reason, scattering angles of light emerging from the measuring object 100 are also important information for the analysis. However, it is known that it is not easy to acquire the information about the scattering angles and it is difficult to solve the transport equation. Therefore, it is conventional practice to use a diffusion equation as diffusion approximation of the transport equation.

However, the foregoing embodiment uses the optical fibers with different numerical apertures as the receiving fibers 12, 13 whereby the optical tomography device can obtain the information about scattering angles of received light, and therefore, when compared with the conventional optical tomography devices, it can obtain more pieces of information about the measuring object 100 and can perform a more detailed analysis using the transport equation.

Figure 2:
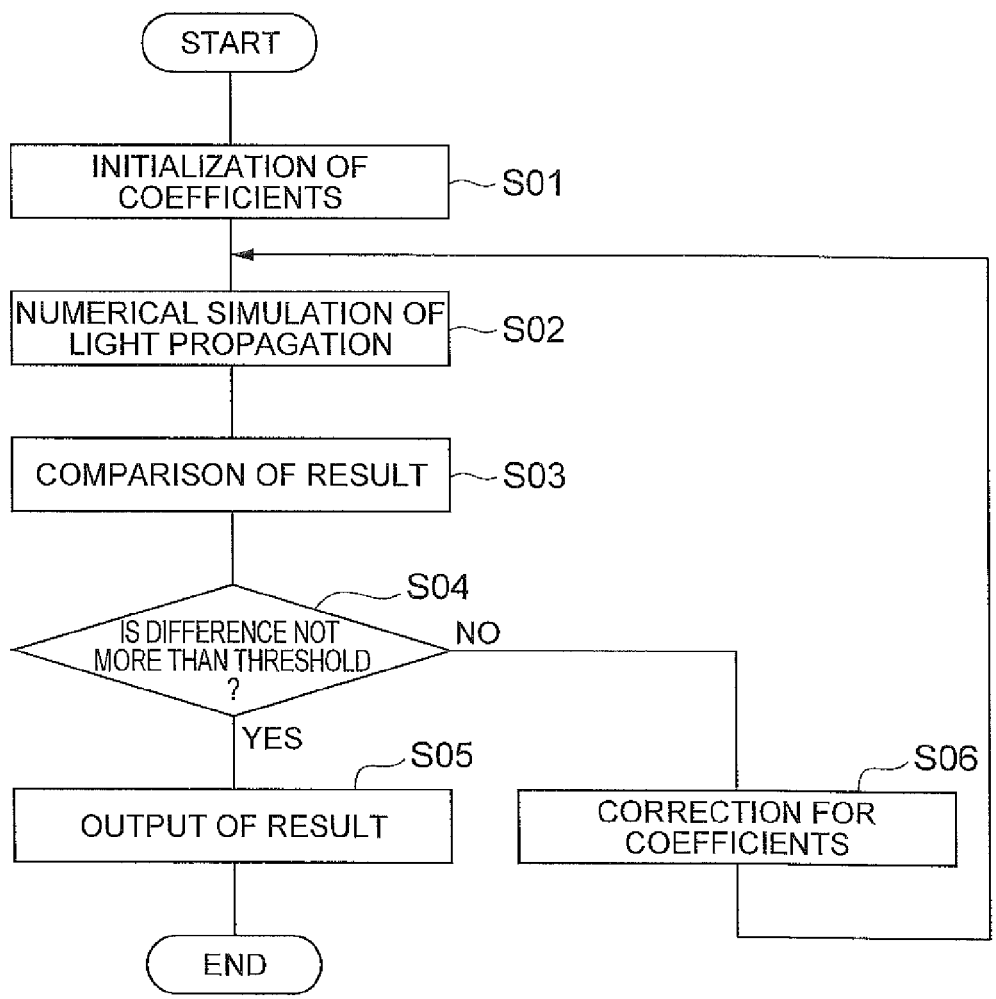
FIG. 2 is a flowchart to illustrate an analysis method by the optical tomography device.

There are two methods available for the analysis by the optical tomography device 1 of the present embodiment, i.e., for the method for calculating the optical characteristic values. One is a method of calculating the optical characteristic values in an inverse problem manner, which is a method of calculating the scattering coefficient, absorption coefficient, and so on by making use of the result of intensities of light obtained by measurement. The other is a method of performing the analysis in a forward problem manner. The below will describe the method of performing the analysis in the forward problem manner, using FIG. 2. FIG. 2 is a flowchart to illustrate the analysis method by the optical tomography device. The process shown in the flowchart of FIG. 2 is carried out by the analysis unit 30 of the optical tomography device 1.

It is first assumed that in the optical tomography device 1, correspondence information of maxima and minima of optical characteristic values of a measuring object, such as the scattering coefficient and the absorption coefficient for each part, is stored for each part included in an interior of the measuring object (i.e., the information is stored in the memory of the analysis unit 30). Then the analysis unit selects information to be used as optical characteristic values of a tissue according to each part of the interior of this measuring object, which are coefficients used in a simulation of light propagation using the transport equation (S01, initialization of coefficients).

Next, the simulation of light propagation in the measuring object is carried out. Specifically, the coefficients initialized in the preceding step are applied to the transport equation to find a calculated value (S02). In this step, the scattering coefficient and absorption coefficient corresponding to each part of the measuring object are applied to the transport equation, in applying the optical characteristic values of the tissue forming the interior of the measuring object, to the transport equation. Then, a comparison is made between this calculated value and a measured value of the measuring object 100 by the optical tomography device 1 (S03). It is then determined whether a difference between the calculated value and the measured value is not more than a predetermined threshold (S04).

When the difference between the calculated value and the measured value is determined to be not more than the threshold, it can be determined that the optical measurement values substituted as initial values into the transport equation are values close to the optical measurement values of each part in the measuring object. On the other hand, when the difference is larger than the threshold, it can be determined that the initial values are inaccurate. Therefore, if the difference between the calculated value and the measured value is determined to be not more than the threshold, this result is sent from the analysis unit 30 to the output unit 40 and the output unit 40 outputs a tomographic image of the measuring object using the analysis result obtained with the application of the optical characteristic values used in the calculation of the calculated value (S05).

On the other hand, when the difference between the calculated value and the measured value is determined not to be not more than the threshold (i.e., when it is determined that the difference is larger than the threshold), a correction is made for the optical characteristic values selected as initial values (S06), the second calculation of calculated value is carried out (S02), a comparison is made between the second calculated value obtained as the result of the calculation and the measured value (S03, S04), and if the comparison result (difference between the calculated value and the measured value) is larger than the threshold, the correction for the coefficients is carried out again (S06). As described above, the device can employ the method of calculating the optical characteristic values by repetitively performing the calculation of calculated value, the comparison between the calculated value and the measured value, and the correction for the coefficients (S02, S03, S04, and S06) until the difference between the calculated value and the measured value becomes smaller than the predetermined threshold.

As described above, the optical tomography device 1 of the present embodiment has the configuration wherein the receiving fibers 12, 13 with different numerical apertures receive two or more kinds of light beams with different solid angle distributions, whereby it can obtain the angular information, in addition to the intensity information of the light emerging from the measuring object 100. As a result, it can enhance the accuracy of the analysis about the tomographic information of the measuring object.

Since the analysis unit 30 of the optical tomography device 1 is configured in the mode of performing the analysis using the transport equation, the foregoing angular information of light can be efficiently utilized, thereby enabling creation of the tomographic information with higher accuracy.

The above described the embodiment of the present invention, and it should be noted that the present invention is not limited only to the foregoing embodiment and can be modified in many ways.

For example, the above embodiment described the optical tomography device 1 having the single irradiation fiber 11 and the two receiving fibers 12, 13 with different numerical apertures, but the numbers can be optionally changed; e.g., it is possible to adopt a mode wherein the number of receiving fibers is three or more and they have three or more different numerical apertures. In this case, since the detection unit 20 detects more pieces of angular information of light, the analysis with much higher accuracy is considered feasible.

It is also possible to adopt a configuration wherein the device is provided with one receiving fiber and a bundle of two irradiation fibers with different numerical apertures. In this case as well, solid angle distributions of light beams emerging from the two irradiation fibers are different, and for this reason, the angular information can be obtained from the light incident into the receiving fiber. Therefore, the accuracy of the analysis about the tomographic information of the measuring object can also be enhanced as in the above embodiment.

It is also possible to adopt a configuration wherein the device is provided with a plurality of sets of the irradiation fiber 11 and the bundle of receiving fibers 12, 13 (or, the receiving fiber and the bundle of multiple irradiation fibers). In this case, it is easy to change the irradiation position of the light from the light source and the reception position, and thus the device can obtain a variety of measurement results though it has the simple device configuration.

Figure 3:
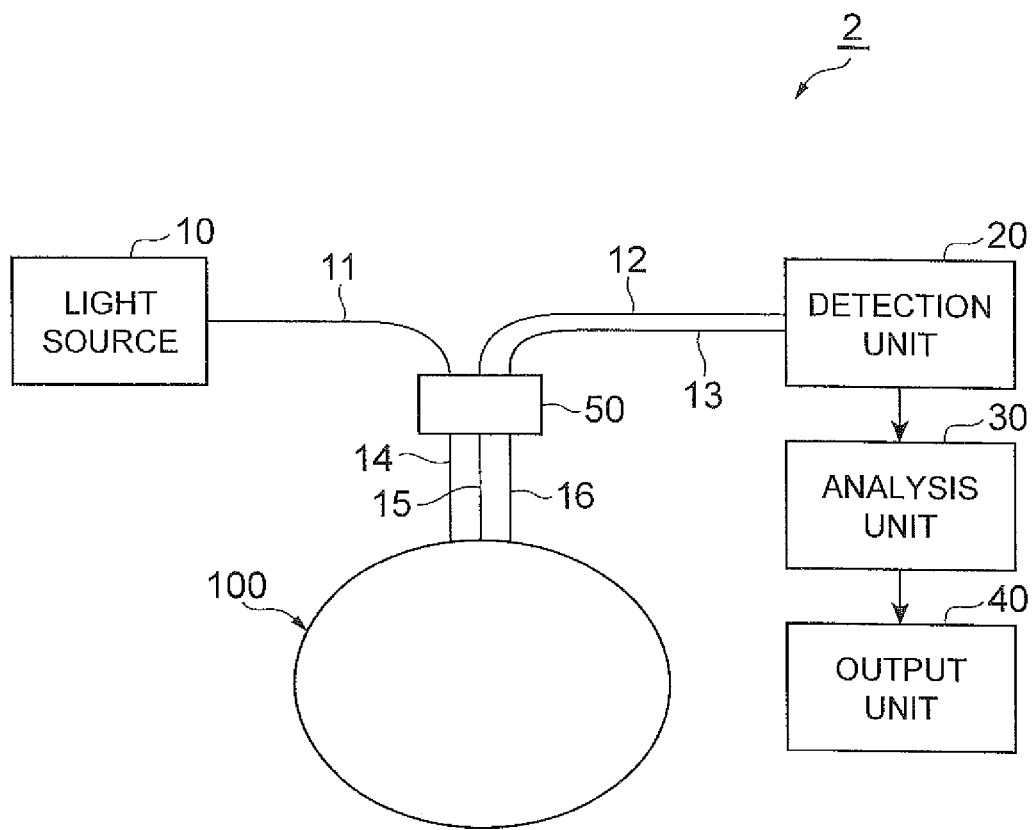
FIG. 3 is a drawing to illustrate a configuration of an optical tomography device according to a modification example.

It is also possible to adopt a configuration wherein one optical fiber is made to function as an irradiation fiber and a receiving fiber. FIG. 3 is a drawing to illustrate a configuration of an optical tomography device 2 according to this modification example. In the optical tomography device 2 shown in FIG. 3, the irradiation fiber 11 and the receiving fibers 12, 13 are connected to a path switching device 50 and three optical fibers 14, 15, and 16 other than the irradiation fiber 11 and the receiving fibers 12, 13 are connected between the path switching device 50 and the measuring object 100. When the device has this configuration, the path switching device 50 switches connections of the irradiation fiber 11 and receiving fibers 12, 13 to the optical fibers 14, 15, 16, for example, in the following manner when the optical fiber 14 is optically connected to the irradiation fiber 11, the optical fiber 14 functions as an irradiation fiber; when the optical fiber 14 is optically connected to the receiving fiber 12, the optical fiber 14 functions as a receiving fiber. In this manner, the provision of the path switching device can achieve simplification of the device (particularly, reduction in the number of optical fibers).

INDUSTRIAL APPLICABILITY

The present invention is applicable to the optical tomography devices capable of obtaining the tomographic information of the measuring object with higher accuracy.

REFERENCE SIGNS LIST 1, 2: optical tomography device; 10: light source; 11: irradiation fiber; 12, 13: receiving fibers; 20: detection unit; 30: analysis unit; 40: output unit; 50: path switching device; 100: measuring object.

The invention claimed is:
1. An optical tomography device comprising:
a light source;
an irradiation fiber for irradiating a measuring object with light from the light source;
a receiving fiber for receiving light emerging from the measuring object in conjunction with irradiation with the light from the irradiation fiber;
a detection unit for detecting an intensity of the light received from the receiving fiber; and
an analysis unit for obtaining an optical characteristic value of an interior of the measuring object, based on the intensity of the light detected by the detection unit,
wherein at least one of the irradiation fiber and the receiving fiber is a bundle in which a plurality of optical fibers are bundled together,
wherein the plurality of optical fibers have two or more different numerical apertures, and
wherein the analysis unit obtains an average of the optical characteristic value in the interior of the measuring object, and a distribution of the optical characteristic value in the interior of the measuring object in order to determine a structure of the interior of the measuring object from the distribution of the optical characteristic value.
2. The optical tomography device according to claim 1, wherein the analysis unit applies the result obtained by the detection unit, to a transport equation as a governing equation governing propagation of light in the measur- ing object, thereby obtaining the optical characteristic value of the interior of the measuring object.

3. The optical tomography device according to claim 1, wherein the optical characteristic value is an absorption coefficient of the interior of the measuring object.

4. The optical tomography device according to claim 1, wherein the optical characteristic value is a scattering coefficient of the interior of the measuring object.

5. The optical tomography device according to claim 1, wherein the optical characteristic value is an anisotropic scattering parameter of the interior of the measuring object.

6. The optical tomography device according to claim 1, wherein the irradiation fiber is the bundle in which the plurality of optical fibers are bundled together, and wherein the optical tomography device comprises a plurality of irradiation fibers.

7. The optical tomography device according to claim 1, wherein the receiving fiber is the bundle in which the plurality of optical fibers are bundled together, and wherein the optical tomography device comprises a plurality of receiving fibers.

8. The optical tomography device according to claim 1, wherein each of the irradiation fiber and the receiving fiber is connected to the light source or the detection unit, and wherein a path switching device implements switching between connections to the light source and to the detection unit.

9. The optical tomography device according to claim 1, wherein the irradiation fiber and the receiving fiber are bundled together in a bundle.

* * * * *